United States Patent
Cacka et al.

(10) Patent No.: US 8,486,029 B2
(45) Date of Patent: Jul. 16, 2013

(54) POT FOR SINUS CAVITY RINSE

(75) Inventors: Joseph W. Cacka, Berthoud, CO (US); Kurt M. Taylor, Fort Collins, CO (US); Kenneth A. Hair, Fort Collins, CO (US); Brian R. Williams, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

(21) Appl. No.: 12/970,610

(22) Filed: Dec. 16, 2010

(65) Prior Publication Data

US 2011/0139824 A1   Jun. 16, 2011

Related U.S. Application Data

(63) Continuation-in-part of application No. 29/352,095, filed on Dec. 16, 2009, now Pat. No. Des. 630,314, and a continuation-in-part of application No. 29/364,670, filed on Jun. 25, 2010, now Pat. No. Des. 676,126.

(60) Provisional application No. 61/287,026, filed on Dec. 16, 2009, provisional application No. 61/369,378, filed on Jul. 30, 2010.

(51) Int. Cl.
*A61M 31/00* (2006.01)

(52) U.S. Cl.
USPC ............................................. 604/275; 604/73

(58) Field of Classification Search
USPC ................ 604/275, 276–279, 73, 82–94, 514
See application file for complete search history.

(56) References Cited

U.S. PATENT DOCUMENTS

| | | | |
|---|---|---|---|
| 465,559 | A | 12/1891 | Good |
| 2,115,959 | A | 5/1938 | Lewis |
| 2,571,921 | A | 10/1951 | Morris |
| 2,578,864 | A | 12/1951 | Tupper |
| D169,996 | S | 7/1953 | Vuillement |

(Continued)

FOREIGN PATENT DOCUMENTS

| | | |
|---|---|---|
| DE | 29602605 | 4/1996 |
| GB | 881807 | 10/1958 |
| WO | WO9629044 | 9/1996 |
| WO | WO2005/000477 | 1/2005 |

OTHER PUBLICATIONS

International Search Report, PCT/US2010/060880, 2 pages, Feb. 14, 2011.

(Continued)

*Primary Examiner* — Kevin C Sirmons
*Assistant Examiner* — Phillip Gray
(74) *Attorney, Agent, or Firm* — Dorsey and Whitney LLP

(57) ABSTRACT

A vessel for use in rinsing a user's nasal cavities includes a main body, a spout extending from the main body, a nozzle attached to the spout, and a handle forming an aperture in communication with the main body. The aperture is sealable by a user to control a flow of a fluid held in the main body out of the nozzle. The nozzle defines an outer skirt deflectable upon engagement with the walls of the user's nasal cavity. A lid is removably engageable with the main body, provides fluid ingress when removed, and creates a watertight seal between the lid and the main body when engaged with the main body. An annular raised periphery may surround the aperture for facilitating sealing of the aperture with the user's finger.

25 Claims, 14 Drawing Sheets

U.S. PATENT DOCUMENTS

| | | | |
|---|---|---|---|
| 2,722,458 A | 11/1955 | Wahlin | |
| 2,811,283 A | 10/1957 | Bowen | |
| 2,987,261 A | 6/1961 | McCuiston et al. | |
| 3,176,883 A | 4/1965 | Davis, Jr. | |
| 3,363,808 A | 1/1968 | Gorman | |
| 3,455,294 A | 7/1969 | Adler et al. | |
| 3,820,532 A | 6/1974 | Eberhardt et al. | |
| 3,847,145 A | 11/1974 | Grossan | |
| 4,083,840 A | 4/1978 | Schoefberger | |
| D250,546 S | 12/1978 | Pick et al. | |
| D250,601 S | 12/1978 | Pick et al. | |
| 4,179,051 A | 12/1979 | Thomas | |
| 4,356,941 A | 11/1982 | McRoskey et al. | |
| D271,028 S | 10/1983 | Adams | |
| 4,439,206 A | 3/1984 | Hildebrand et al. | |
| 4,489,535 A | 12/1984 | Veltman | |
| 4,513,891 A | 4/1985 | Hain et al. | |
| 4,526,797 A | 7/1985 | Stone, Jr. | |
| 4,555,469 A | 11/1985 | Erdmann et al. | |
| 4,760,937 A | 8/1988 | Evezich | |
| D305,262 S | 12/1989 | Nichols | |
| 4,925,128 A | 5/1990 | Brody | |
| D314,702 S | 2/1991 | Gonzalez | |
| D317,940 S | 7/1991 | Brenner | |
| 5,301,846 A | 4/1994 | Schmitz | |
| 5,316,054 A | 5/1994 | Hall et al. | |
| 5,330,634 A | 7/1994 | Wong et al. | |
| 5,354,849 A | 10/1994 | Schoefberger | |
| 5,505,193 A | 4/1996 | Ballini et al. | |
| 5,570,966 A | 11/1996 | Phelan | |
| 5,611,376 A | 3/1997 | Chuang | |
| 5,655,686 A | 8/1997 | Jermyn | |
| D390,744 S | 2/1998 | Otero | |
| 5,806,723 A | 9/1998 | DuBose | |
| D405,525 S | 2/1999 | Barrett et al. | |
| 5,897,872 A | 4/1999 | Picciano | |
| 5,899,878 A | 5/1999 | Glassman | |
| 5,967,377 A | 10/1999 | Glynn | |
| 6,006,952 A | 12/1999 | Lucas | |
| 6,035,769 A | 3/2000 | Nomura et al. | |
| D424,197 S | 5/2000 | Sydlowski et al. | |
| D426,300 S | 6/2000 | Conforti | |
| 6,135,358 A | 10/2000 | Ballini | |
| 6,238,377 B1 | 5/2001 | Liu | |
| 6,241,705 B1 * | 6/2001 | Ko-Wen | 604/73 |
| 6,293,436 B2 | 9/2001 | Faughnder et al. | |
| 6,520,384 B2 | 2/2003 | Mehta | |
| 6,540,718 B1 | 4/2003 | Wennek | |
| 6,558,344 B2 | 5/2003 | McKinnon et al. | |
| D481,794 S | 11/2003 | Krinsky | |
| 6,669,059 B2 | 12/2003 | Mehta | |
| D486,066 S | 2/2004 | Hannen et al. | |
| 6,688,497 B2 | 2/2004 | Mehta | |
| 6,736,792 B1 | 5/2004 | Liu | |
| D490,896 S | 6/2004 | Bogazzi | |
| D493,888 S | 8/2004 | Reschke | |
| D495,954 S | 9/2004 | Solomon | |
| D497,107 S | 10/2004 | Hama et al. | |
| 6,814,259 B1 | 11/2004 | Foster et al. | |
| 6,907,879 B2 | 6/2005 | Drinan et al. | |
| D530,815 S | 10/2006 | Murphy et al. | |
| D538,474 S | 3/2007 | Sheppard et al. | |
| D548,334 S | 8/2007 | Izumi | |
| D550,097 S | 9/2007 | Lepoitevin | |
| 7,306,121 B2 | 12/2007 | Ophardt et al. | |
| D558,509 S | 1/2008 | Bodum | |
| D558,510 S | 1/2008 | Bodum | |
| D562,404 S | 2/2008 | Jansen et al. | |
| D584,151 S | 1/2009 | Murphy | |
| 7,500,584 B2 | 3/2009 | Shutz | |
| D590,493 S | 4/2009 | Harlan et al. | |
| D601,697 S | 10/2009 | Sobiech et al. | |
| D603,708 S | 11/2009 | Handy | |
| D608,645 S | 1/2010 | Handy et al. | |
| D612,736 S | 3/2010 | Pecora | |
| D613,601 S | 4/2010 | Yoneda | |
| 7,703,696 B2 | 4/2010 | Eddins et al. | |
| D627,458 S | 11/2010 | Bisson et al. | |
| D629,884 S | 12/2010 | Stephens | |
| D630,314 S | 1/2011 | Stephens | |
| 7,862,536 B2 | 1/2011 | Chen et al. | |
| D634,213 S | 3/2011 | Thompson | |
| D634,630 S | 3/2011 | Taylor | |
| D634,631 S | 3/2011 | Taylor | |
| 7,959,597 B2 | 6/2011 | Baker et al. | |
| D653,953 S | 2/2012 | Wakeman | |
| 2003/0062367 A1 | 4/2003 | Robinson et al. | |
| 2005/0049620 A1 | 3/2005 | Chang | |
| 2006/0008373 A1 | 1/2006 | Schutz | |
| 2008/0008979 A1 | 1/2008 | Thomas et al. | |
| 2008/0294124 A1 | 11/2008 | Mehta | |
| 2009/0234325 A1 | 9/2009 | Rozenberg et al. | |
| 2009/0281454 A1 | 11/2009 | Baker et al. | |
| 2011/0139149 A1 | 6/2011 | Cacka et al. | |
| 2011/0139826 A1 | 6/2011 | Hair et al. | |
| 2011/0144588 A1 | 6/2011 | Taylor et al. | |
| 2011/0184341 A1 | 7/2011 | Baker et al. | |
| 2001/0319840 | 12/2011 | Hair | |

OTHER PUBLICATIONS

International Search Report, PCT/US2010/060882, 2 pages, Feb. 16, 2011.

Author Unknown, "NasaFlo Neti Pot," http://www.neilmed.com/usa/nasaflo.php, 1 page, at least as early as Dec. 9, 2009.

Author Unknown, "SinuFlo Ready Rinse," http://www.neilmed.com/usa/sinuflo.php, 1 page, at least as early as Dec. 9, 2009.

Author Unknown, "Sinus Rinse Nasal Wash," http://www.neilmed.com/usa/sinusrinse.php, 3 pages, at least as early as Dec. 9, 2009.

Papsin et al., "Saline Nasal Irrigation," Canadian Family Physician, vol. 49, pp. 168-173, Feb. 2003.

Rabago et al., "Efficacy of Daily Hypertonic Saline Nasal Irrigation Among Patients with Sinusitus: A Randomized Controlled Trial," The Journal of Family Practice, vol. 51, No. 12, pp. 1049-1055, Dec. 2002.

Schumann et al., "Patients Insist on Antibiotics for Sinusitus? Here is a Good Reason to Say 'No'," The Journal of Family Practice, vol. 57, No. 7, pp. 464-468, Jul. 2008.

\* cited by examiner

POT FOR SINUS CAVITY RINSE

CROSS-REFERENCE TO RELATED APPLICATIONS

This application claims the benefit of priority under 35 U.S.C. §120 as a continuation-in-part of U.S. design application No. 29/352,095 entitled "Vessel with handle for sinus cavity rinse" filed 16 Dec. 2009 and as a continuation-in-part of U.S. design application No. 29/364,670 entitled "Faceted nasal seal" filed 25 Jun. 2010, the disclosures of which are hereby incorporated herein by reference in their entireties. This application claims the benefit of priority pursuant to 35 U.S.C. §119(e) of U.S. provisional application No. 61/287,026 entitled "Vessel for sinus cavity rinse" filed 16 Dec. 2009 and U.S. provisional application No. 61/369,378 entitled "Faceted nasal seal" and filed 30 Jul. 2010, the disclosures of which are hereby incorporated herein by reference in their entireties.

This application is related to the application entitled "Bottle for sinus cavity rinse" filed contemporaneously herewith having 12/970,788; the application entitled "Powered irrigator for sinus cavity rinse" filed contemporaneously herewith having 12/970,345; the application entitled "Faceted nasal seal" filed contemporaneously herewith having 12/970,854; and the application entitled "Squeeze bottle for sinus cavity rinse" filed contemporaneously herewith having 12/970,415, the disclosures of which are incorporated herein by reference in their entireties.

TECHNOLOGY FIELD

This invention relates to a vessel for nasal cavity rinse having a soft, self-sealing nozzle and a finger or thumb-actuated valve for controlling the flow of the liquid from the vessel.

BACKGROUND

The benefits of rinsing one's sinus cavities have been well established, and include improving resistance to sinus infections, clogged sinuses, allergies, and general health. Oftentimes, however, the articles which one uses to rinse their nasal passages make the process unnecessarily difficult and uncomfortable. One of the issues is related to the inability to obtain an effective seal between the nozzle of one of these articles and the user's nasal passage. If the seal is not adequate, during use the fluid can leak from between the nozzle and the nasal passage, thereby making the rinsing process messy.

In addition, the control of the flow from the vessel into the sinus cavity has not been adequate in the past, and users have found it difficult to regulate the volume of flow so as to make the rinsing process comfortable. In one existing product, as shown in U.S. App. Pub. No. 2008/0294124, an aperture is formed in the lid of the vessel which can be used to restrict the flow of the fluid in the vessel through the nozzle during the rinsing step. However, because the aperture is positioned in the lid, the user uses one hand to hold the vessel and another hand to control the flow by covering and uncovering the aperture. This proves to be a relatively difficult process when the user is already in an awkward position, such as being positioned over a sink during the rinsing process.

The information included in this Background section of the specification, including any references cited herein and any description or discussion thereof, is included for technical reference purposes only and is not to be regarded subject matter by which the scope of invention is to be bound.

SUMMARY

In one implementation, a vessel for use in rinsing a user's nasal passage includes a main body, a spout extending from the main body, a nozzle attached to the spout, and a handle forming an aperture in communication with the main body, where the aperture formed in the handle is sealable by a user to control a flow of a fluid held in the main body out of the nozzle.

In another implementation, a vessel includes a main body forming a cavity for receiving a fluid; a spout extending off a front portion of the main body; an elastomeric nozzle attached to the spout; a handle extending off a back portion of the main body opposite the front portion; and an aperture formed in the handle in communication with the cavity by way of the partially hollow handle. The elastomeric nozzle defines an outer skirt deflectable upon engagement with the walls of the user's nasal cavity. The handle is partially hollow and in communication with the cavity formed by the main body. The aperture is for use in controlling a flow of the fluid positioned in the vessel out of the nozzle.

In a further implementation, a vessel for use in rinsing a user's nasal passage includes a main body forming a cavity for receiving a fluid and an opening for allowing the fluid to enter the cavity; a lid removably positioned over the opening and engageable with the main body to create a watertight seal between the lid and the main body; a spout extending off the main body; an elastomeric nozzle detachably coupled to the spout; a handle extending off the main body; an aperture formed in a top portion of the handle in communication with the cavity by way of the at least partially hollow handle; and an annular raised periphery surrounding the aperture and extending from the top portion of the handle. The elastomeric nozzle defines an outer skirt deflectable upon engagement with the walls of the user's nasal cavity. The handle is at least partially hollow and in communication with the cavity formed by the main body. The aperture is for use in controlling a flow of the fluid in the main body out of the nozzle. The raised periphery is for facilitating sealing of the aperture with the user's finger.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the invention as claimed herein will be apparent from the following more particular written description of various embodiments of the invention as further illustrated in the accompanying drawings and defined in the appended claims.

DETAILED DESCRIPTION

An exemplary implementation of a vessel 100 for use in performing a sinus rinse is shown in FIGS. 1 through 12. The vessel 100 includes features that allow it to function in a beneficial manner for a user, including a self-sealing nozzle 110 to help ensure an adequate liquid seal between the user's nasal passage and the nozzle, as well as a flow control aperture 112 easily manipulated by the user to allow some control of the liquid flow during the nasal rinsing procedure. In this example, the flow control aperture 112 is positioned on the handle 114 within easy reach of the user's thumb while grasping the handle 114 of the vessel 100.

Figure 1:
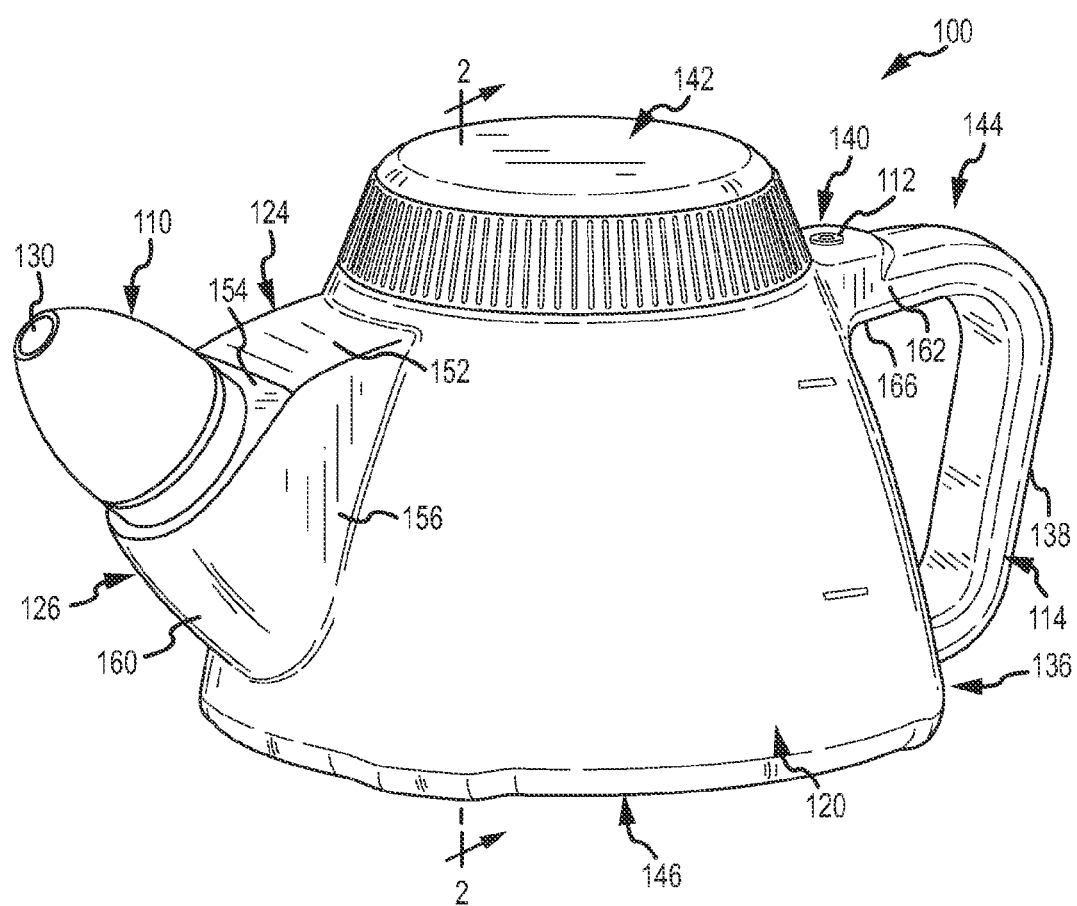
FIG. 1 is an isometric view of a vessel for sinus cavity rinse and includes a main body, handle, a lid, a spout, a nozzle, and a flow control aperture.
Figure 2:
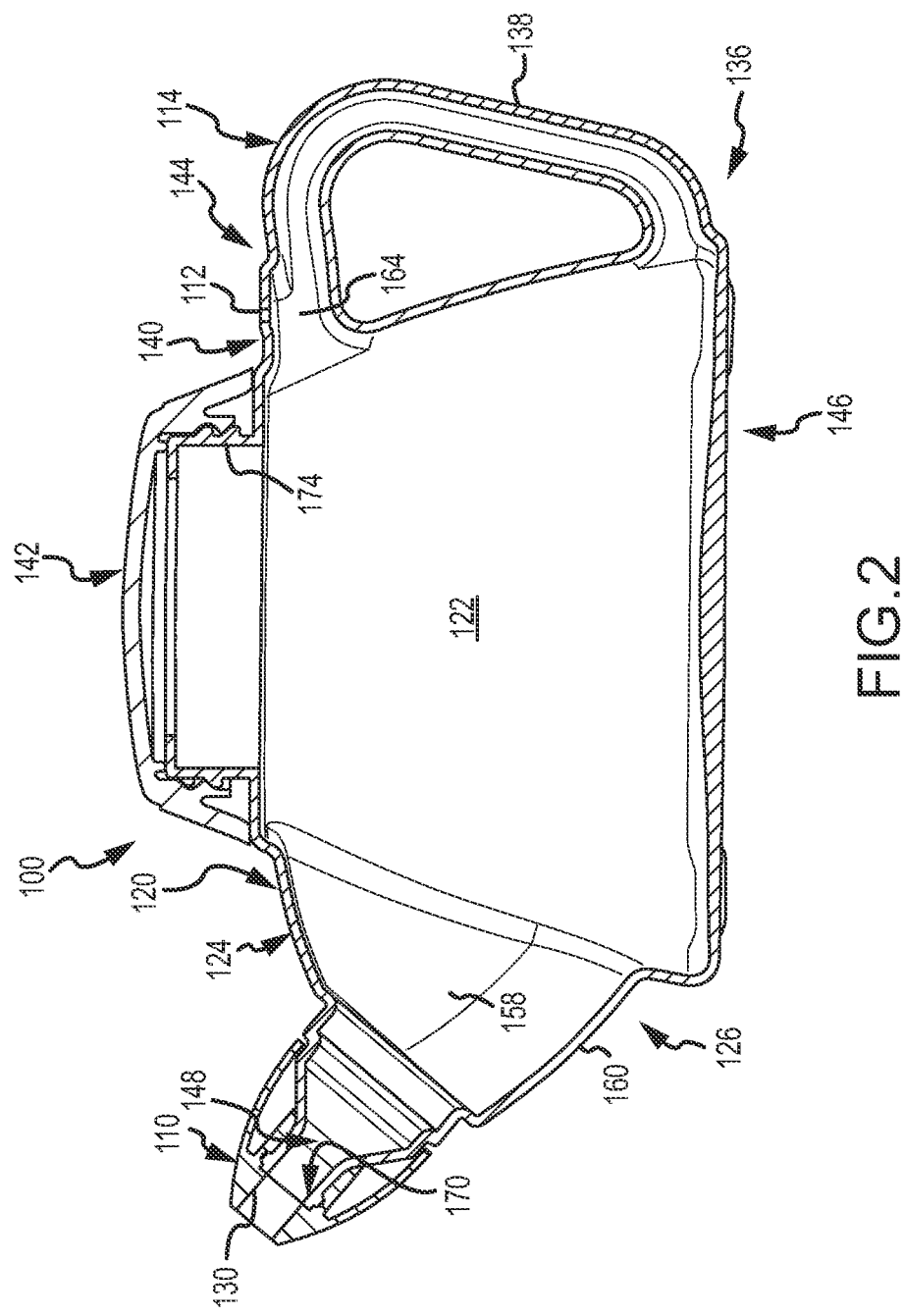
FIG. 2 is a cross-section view of FIG. 1 taken along line 2-2 in FIG. 1.

FIGS. 1 and 2 show the vessel 100 for sinus rinsing, which includes a main body 120 defining a cavity 122 for receiving a liquid, such as a sinus rinsing solution. A spout 124 is formed and extends off a front portion 126 of the main body 120 of the vessel with a self-sealing nozzle 110 positioned at a terminal end of the spout 124. The nozzle 110 includes an opening 130 through which the fluid inside the cavity 122 of the vessel may pass when the vessel 100 is tipped to allow the water to flow into the spout 124 and out of the nozzle opening 130. The handle 114 extends from the opposite or back portion 136 of the vessel and provides a suitable gripping portion 138 for a user to easily lift and control the orientation of the vessel. The handle 114 with gripping portion 138 is hollow and is open to the cavity 122 formed by the main body 120 of the vessel 100.

A top portion 140 of the main body 120 defines a large opening through which the cavity 122 of the vessel is filled with solution. A lid 142 is removably engaged to the main body 120 of the vessel and is configured to be positioned over the large opening of the main body 120 in order to provide a watertight and airtight seal between the lid 142 and the main body 120. A flow control aperture 112 is formed in the handle 114 near the intersection of the top portion 144 of the handle with the main body 120 of the vessel. The flow control aperture 112 is positioned on the top portion 144 of the handle 114 for easy manipulation by the user's thumb. The top portion 144 of the handle extends from a top portion 140 of the main body and extends laterally outwardly and then bends downwardly to reconnect with the bottom portion 146 of the main body, and generally forms an inverted triangular shape. The handle 114 may thus be partially hollow at the aperture 112, or the handle 114 may be hollow along its entire length from where it connects the top portion 140 of the main body to where the handle 114 connects to the bottom portion 146 of the main body 120.

The spout 124, which includes an end portion 148 to which the nozzle is attached, also has a roughly triangular shape and is open to and communicates with the cavity 122 of the main body 120 from near the bottom of the lid 142 down to near the bottom of the main body 120. The spout 124 has a generally rectangular cross-section as it extends from the main body 120 and has a rectangular-shaped top surface 152 extending from the main body 120, an angled surface 154 which extends from the top surface 152 from which the end portion 148 extends at a right angle for receiving the nozzle 110 (see FIG. 5). Two opposite side portions 156, 158 engage along the side of the main body 120 and connect together at a radius 160 at the bottom of the spout 124.

In one exemplary implementation, the vessel 100 may be made of high density polyethylene (HDPE), and can be opaque or translucent. It is helpful if the sidewalls of the main body 120 are translucent so the user can see the level of the fluid inside the vessel.

The flow control aperture 112 may be positioned at any point on the handle 114 that is easily manipulable by the user's fingers or thumb. For example, while the flow control aperture 112 is shown on the top surface 144 of the handle 114, it may also be on either side surface 162, 164 (see FIG. 2) of the handle 114, or on the bottom surface 166 of the handle 114. If on the side surface 162, 164 of the handle 114, the flow control aperture 112 may be actuated by a user's thumb or forefinger, depending on the side on which it is positioned. If the flow control aperture 112 is on the bottom surface 166 of the top portion of the handle, 114 it may be controlled by the user's forefinger. The flow control aperture 112 may also be positioned at other locations along the length of the handle 114. Also, the flow control aperture 112 may be circular, square, trapezoidal, oval, or irregular in shape, as long as its size allows it to be entirely covered by the user's finger or thumb.

FIG. 2 shows the vessel 100 in cross-section. The cavity 122 formed by the vessel extends through the handle 114, as well as into the spout 124 and through the nozzle 110. The cavity does 122 not have to extend entirely through the handle, as long as the portion of the handle that has the flow control aperture 112 formed in it is exposed to the cavity 122. The rest of the handle 114 may be solid. In the exemplary embodiment shown, the vessel 100 is blow-molded, which makes it relatively easy to form a hollow handle.

An engagement structure 170 between the self-sealing nozzle 110 and the end portion 148 of the spout 124 is also shown in FIG. 2. The engagement structure 170 allows the nozzle 110 to be securely positioned on the spout 124, yet allows the nozzle 110 to self adjust its size to the size of the user's nasal passage during use as discussed in more detail below. Additionally, FIG. 2 shows the lid 142 structure threaded onto a collar 174 extending from the top portion 140 of the main body of the vessel. The lid 142 seals in an airtight and watertight manner with the collar 174 in order to allow the flow control aperture 112 to best perform. This structure will be further described in some detail below.

Figure 3:
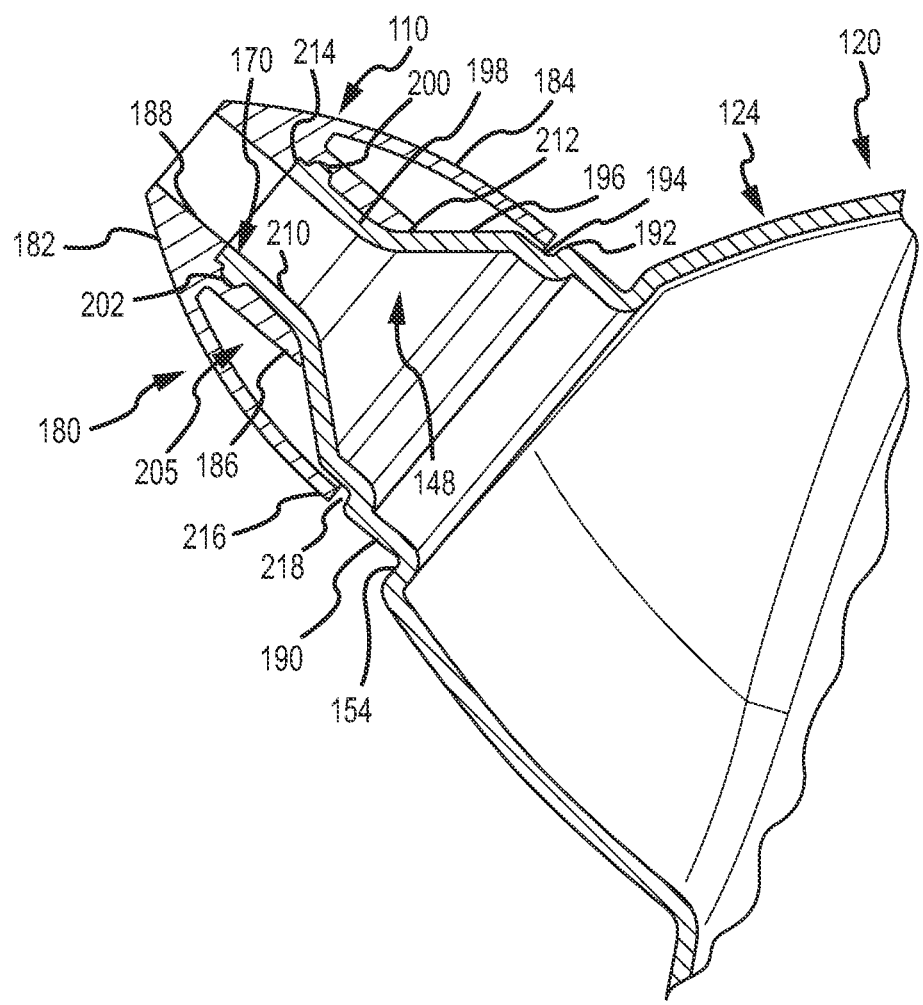
FIG. 3 is an enlarged cross-section view similar to that of FIG. 2, focusing on the nozzle and spout of the vessel.

FIG. 3 depicts an enlarged cross-section view of the self-sealing nozzle 110 connected with the end portion 148 of the spout 124. The self-sealing nozzle 110 has a main body 180, including a user engagement tip 182, an outer skirt 184 formed by a wall extending downwardly and outwardly away from the tip 182, and an inner collar 186 extending downwardly and away from the tip 182. In one exemplary embodiment, the inner collar 186 may have a wall thickness of approximately 0.060 inches. An aperture 188 passes through the tip 182 and the inner collar 186 of the nozzle. The inner collar 186 has a terminal edge, as does the outer skirt 184. In one exemplary embodiment, the outer skirt 184 may have a wall thickness of approximately 0.040 inches. The outer skirt 184 may be smoothly curved in the generally conical shape as shown, or may be faceted or otherwise made up of regions having flat extensions or mixed flat and curved extensions. Also, a rib may be formed on the outer surface around the skirt 184 wall just above the bottom edge to provide a protrusion for enhancing a user's gripping force on the nozzle if necessary.

The end portion 148 extends or protrudes upwardly from the angled top surface 154 of the spout 124 and receives the nozzle 110. The end portion 148 includes a base section 190 having a first diameter, a shoulder 192 formed annularly around the base section 190 extending to a decreased diameter to form a first portion 194 of the end portion 148. The first portion 194 transitions into the conical section 196, extending further away from the base section 190 and tapering and decreasing in diameter even further until transitioning into the second portion 198. The second portion 198 forms a cylindrical wall and extends away from the conical section 196. An annular rib 200 is formed on the outer diameter of the second portion 198. The base section 190, first portion 194 and the second portion 198 are generally cylindrical in shape, with the inner diameters and outer diameters being largest at the base portion 190, somewhat smaller for the second portion 194, decreasing with the angle of the conical section 196, down to the size of the second portion 198.

The outer diameter of the second portion 198 that has the annular rib 200 is about the same diameter as the inner diameter of the inner collar 186 of the nozzle such that when the nozzle 110 is positioned over the second portion 198, the inner collar 186 of the nozzle engages the outer walls of the second portion 198, and the rib 200 of the second portion snaps into the annular channel 202 formed in the inner diameter of the inner collar 186 to hold the nozzle 110 onto the end portion 148 at a predefined position. This engagement structure 170 allows secure placement of the nozzle 110 on top of the end portion 148, but allows it to be removed for cleaning or replacement if desired.

When the nozzle 110 is positioned on the end portion 148, the aperture 188 of the engagement tip 182 of the nozzle aligns with the aperture 210 formed in the second portion 198 of the end portion 148 of the spout 124. The terminal edge 212 of the inner collar 186 of the nozzle may engage the outer wall of the conical section 196 somewhat near the intersection between the conical section 196 and the second portion 198 of the end portion of the spout. The terminal edge 212 of the inner collar 186 may be beveled at an angle complementary to the angle of the conical section 196 of the spout 124 to connect with the conical section 196 and to provide additional sealing. The engagement of the terminal edge 212 of the inner collar 186 provides sealing to help keep the fluid flowing through the end portion 148 and the nozzle 110 and from passing between the engagement of the nozzle 110 and the second portion 198.

In the predefined position of the nozzle 110, the end of the second portion 198 also engages a shoulder 214 formed in the tip 182 of the nozzle 110. The shoulder 214 is formed around the aperture 188 extending through the tip 182. The tip 182 of the nozzle may be solid in the area surrounding the aperture 188 extending through the tip. However, the outer wall extending downwardly and away from the tip 182 forms an outer skirt 184, starting at about the position from where the inner collar 186 extends downwardly from the base of the tip 182. An annular space or void 205 is formed between the outer skirt 184 and the inner collar 186 and between the outer skirt 184 and the conical section 196. That is, the void space 205 is formed in the area of the nozzle 110 where the outer skirt 184 and the inner collar 186 extend down. Because the wall forming the outer skirt 184 extends further from the tip 182 than the wall forming the inner collar 186 does, the void 205 is also formed between the skirt 184 and the conical section 196 beyond the terminal edge 212 of the inner collar 186.

The terminal edge 216 of the skirt 184 is positioned around the first portion 194 of the end portion of the spout 124. The terminal edge 216 of the skirt, as well as the adjacent wall structure of the skirt 184, closely fits with the first portion 194 of the end portion, but does not necessarily engage the first portion 194. Also, a gap 218 may be formed between the shoulder 192 extending between the base portion 190 and the first portion 194 and the terminal edge 216 of the skirt 184. The terminal edge 216 of the skirt 184 does not attach to or otherwise affix to the spout 124 and may move relative thereto. The inner collar 186 connects to the end portion 148 at a position closer to the tip 182 of the nozzle 110 and is spaced above the edge of the outer skirt 184.

The nozzle 110 may be made of a soft elastomeric material, for example, food grade silicone rubber. The skirt 184, when positioned in the user's nasal passage, flexes inwardly into the void space 205 formed between the skirt 184 and the inner collar 186 and the void space 205 between the skirt 184 and the conical section 196 and may do so radially and/or irregularly around its circumference in order to closely match the shape of the user's nostril. This helps create an adequate seal between the user's nostril and the self-sealing nozzle structure. When the nozzle 110 is removed from the user's nostril, the elastomeric material springs back into its original shape. In one exemplary implementation, the wall thickness of the skirt 184 may be 0.040 inches and the wall thickness of the inner collar 186 may be 0.060 inches. The gently curving, cone-like shape of the nozzle 110 from the tip 182 down to the terminal edge 216 of the skirt 184 allows for a close fit with a variety of sizes of nasal passages. The void space 205 may be annular, or may be discontinuous within the skirt wall.

One feature that allows the structure of the skirt 184 to provide an adequate seal for the user's nasal passages is the engagement of the terminal edge 216 of the skirt with the first portion 194 of the spout end portion 148. When the nozzle 110 is inserted into the user's nasal passage, and the skirt 184 compresses radially inwardly to conform to the shape of the user's nasal passage, the terminal end 216 of the skirt 184 engages the first portion 194 of the spout end portion 148 and keeps that portion of the skirt 184 from deflecting further inwardly, thus providing some structural rigidity to the flexion of the portion of the skirt 184 extending between the tip 182 and the terminal edge 216. This provides some resistance to flexure to help create a firm but comfortable fit of the nozzle 110 within the user's nasal passage, and also facilitates the rebound of the skirt 184 back to its original shape after being removed from the user's nasal passage. However, the terminal end 216 is not joined to the spout 124 and may move relative to the spout 124.

Figure 4:
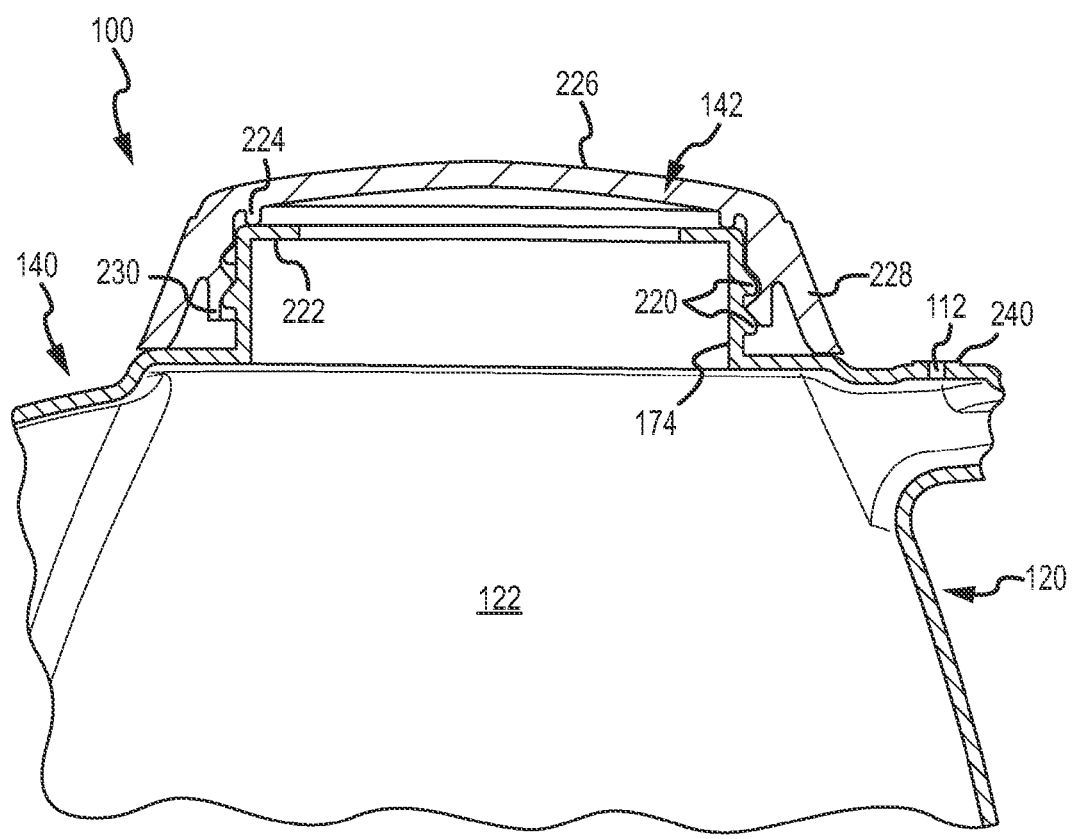
FIG. 4 is an enlarged cross-section view similar to that of FIG. 2, focusing on the lid structure.
Figure 5:
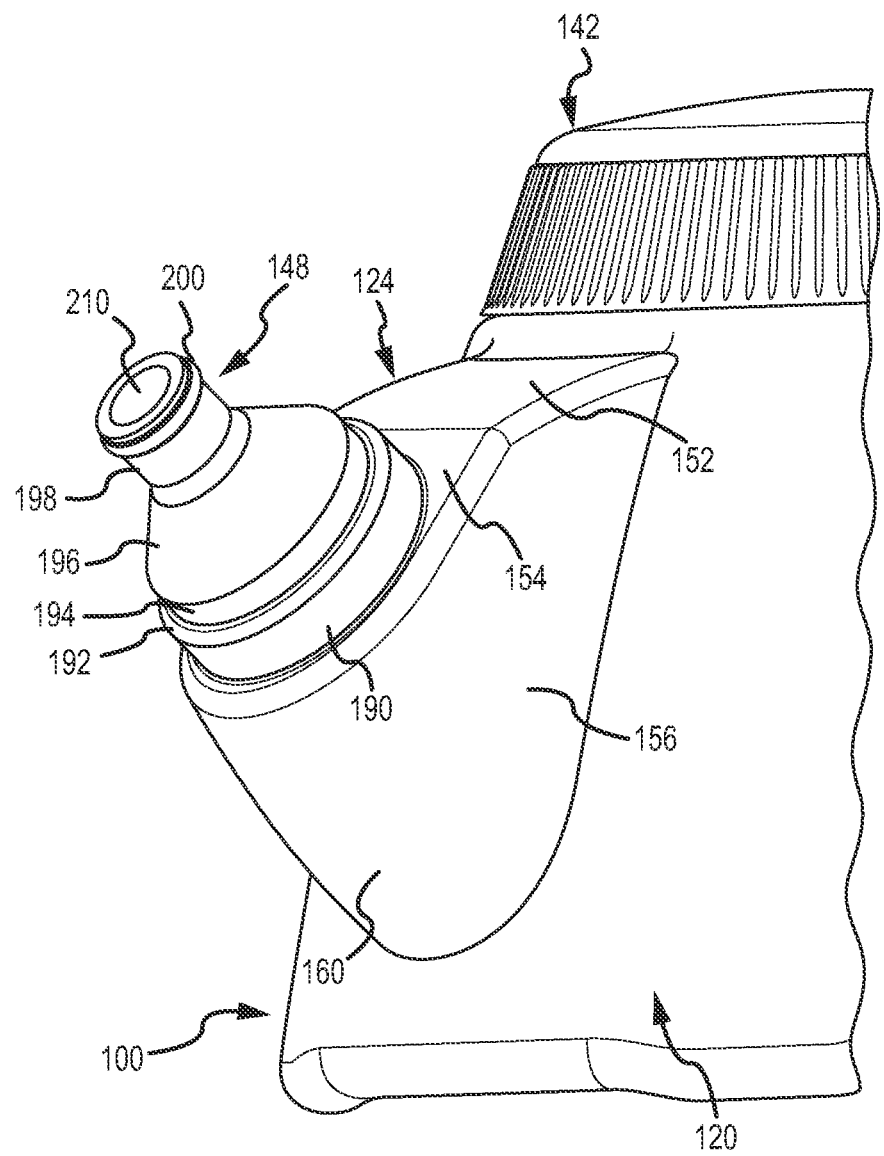
FIG. 5 is an enlarged, isometric view of the spout of the vessel with the nozzle removed.
Figure 6:
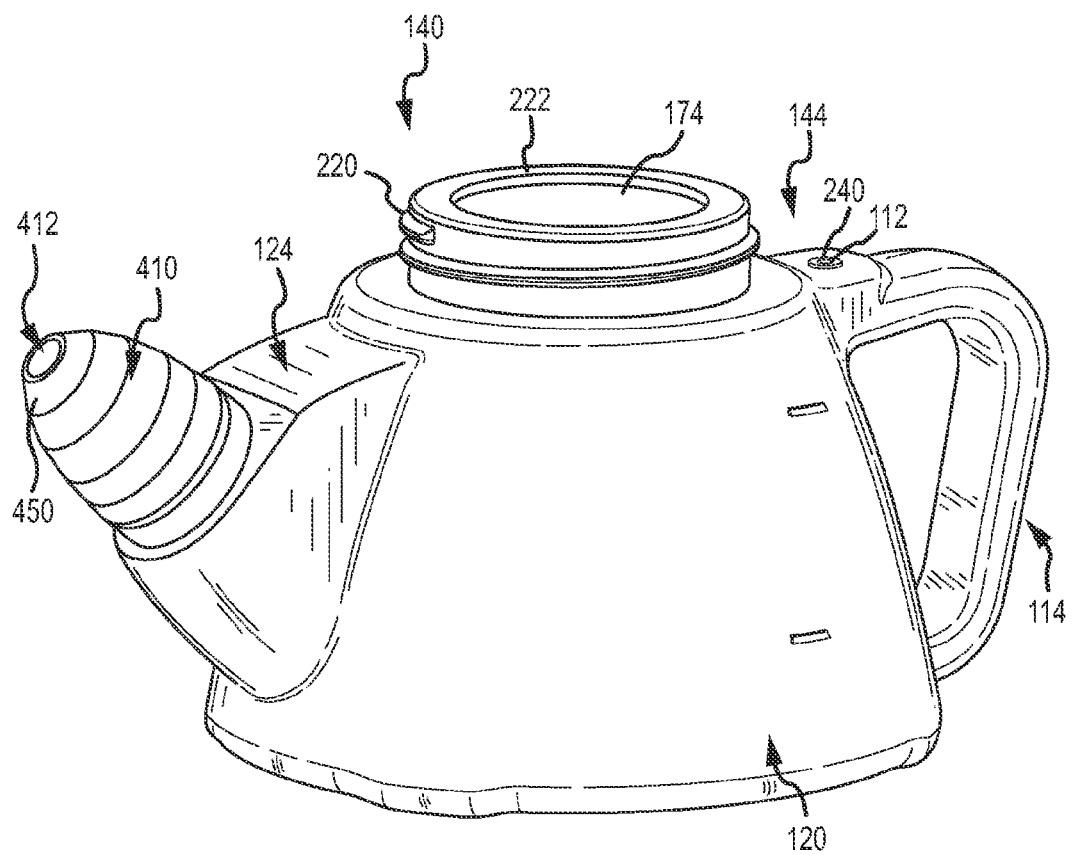
FIG. 6 is an isometric view of the vessel with another embodiment of a nozzle and with the lid removed.
Figure 7:
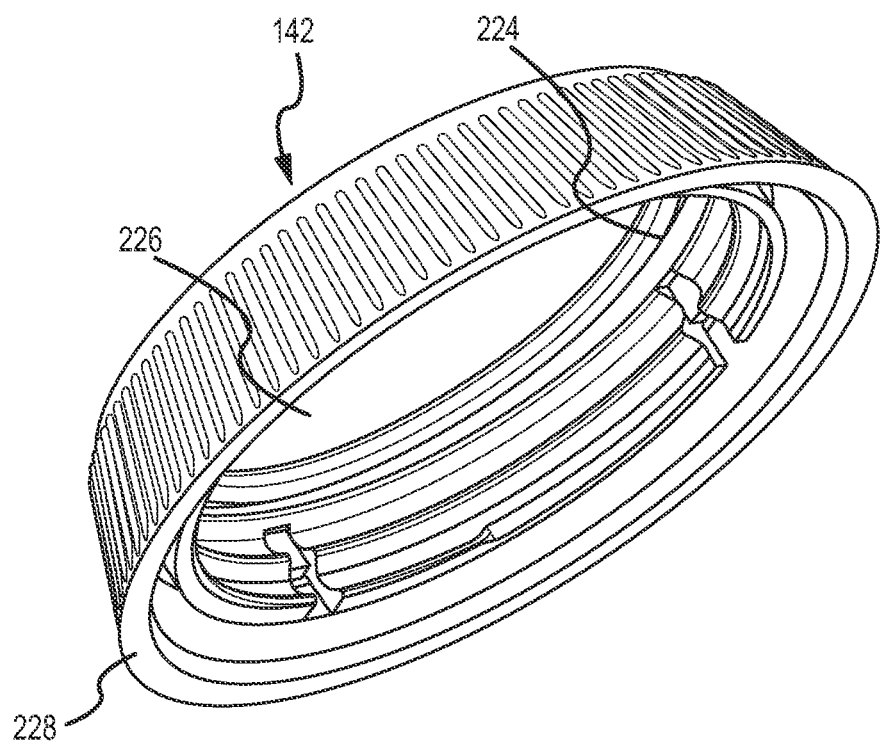
FIG. 7 is a bottom isometric view of the lid.
Figure 8:
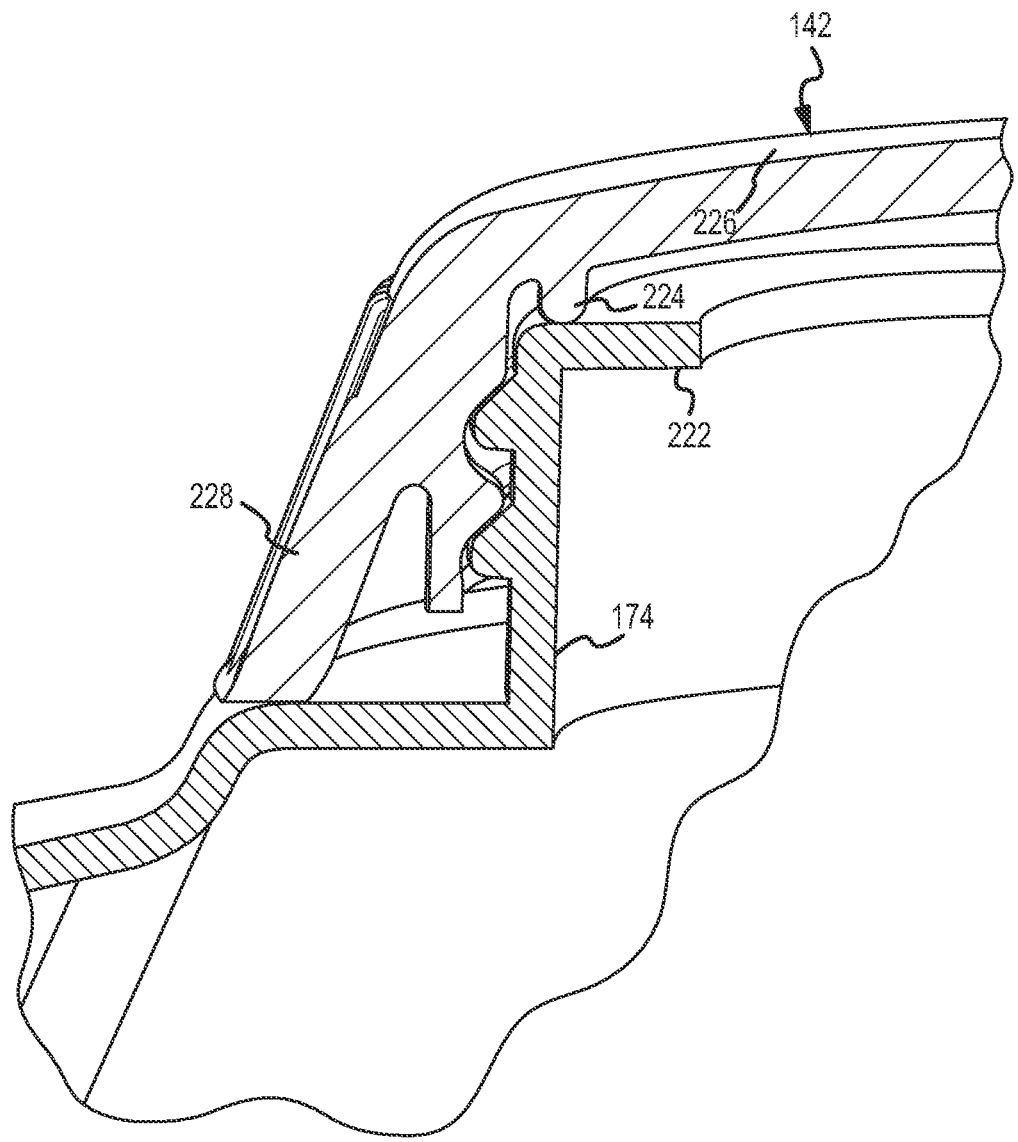
FIG. 8 is an enlarged, cross-section view similar to FIG. 4, focusing on the engagement of the lid with the vessel collar.

FIG. 4 shows an enlarged section view of the lid 142 in a sealed engagement with the top portion 140 of the vessel 100. As shown in FIGS. 4 and 6, the top portion 140 of the vessel forms an opening defined by a collar 174. Threads 220 are formed on the outer perimeter of the collar 174 for threadedly receiving the lid 142 and sealing element provided as a seal flange 222 extends radially inwardly from the top of the collar 174 for engagement with the seal rim 224 of the lid 142, as described below, to facilitate an airtight and a watertight seal between the lid 142 and the seal flange 222. The lid 142, as shown in FIGS. 4, 7 and 8, includes a top portion 226 from which a flange 228 depends downwardly as shown in FIG. 4. The threads 230 are formed on the inner diameter of the seal flange 228 and correspond to the threads 220 on the collar of the vessel 100 to form a threaded engagement and removably secure the lid 142 to the collar 174. The seal rim 224 extends downwardly from the top portion 226 of the lid and has an annular shape to engage the top surface of the seal flange 222 when the lid 142 is fully threaded onto the collar 174 of the vessel 100. The seal rim 224 engaging the seal flange 222 facilitates providing or creating an airtight and/or a watertight seal. In certain implementations, the lid 142 may not establish an airtight and a watertight seal at the collar 174 and instead even if the seal rim 224 is in engagement with the collar 174 there may be some water leakage or air leakage between the seal rim 224 and the collar 174. In other implementations, while a watertight seal may not be provided, the seal rim 224 and the seal flange 222 may establish a substantially airtight seal to allow a user sealing and unsealing the aperture 112 to efficiently operate the starting and stopping of fluid flow from the vessel 100, described further below.

FIGS. 1, 4 and 6 also show a raised periphery 240 of the aperture 112 where it is positioned in the handle 114. The raised periphery 240 is shown as having an annular shape surrounding the aperture 112 and the raised surface is substantially flat. The raised periphery 240 provides an annular tactile location for the user during the rinsing procedure so it is easier for the user to find the aperture 112 while they are busy performing the rinse procedure. Also, the relief formed by the raised periphery 240 of the flow control aperture 112 also helps provide a better seal with less pressure between the user's finger or thumb and the rim of the aperture 112. In some implementations, the surface of the raised periphery 240 may not be annularly shaped, and for example, may have the same shape as an aperture having a shape other than circular, e.g., square, trapezoidal, oval, or irregular in shape. In other implementations, the raised periphery 240 may have a shape that differs from the aperture 112, and for example may be annularly shaped while the aperture 122 has an oval shape. Implementations including more than one aperture 112 may include a raised periphery around each aperture 112, or where one aperture 112 is arranged side-by-side with another aperture 112, the raised periphery 240 may surround each of the apertures.

FIG. 6 also shows the vessel 100 with a faceted nozzle 410 having a faceted surface that allows the faceted nozzle 410 to create a seal within the nasal cavity better than an oval or purely round nozzle. As described further below in connection with FIGS. 12-14, the faceted or circumferentially stepped nozzle external surface is made up of regions having flat extensions or mixed flat and curved extensions, as the faceted nozzle 410 extends downwards. Like the nozzle 110, the faceted nozzle 410 is self-sealing and is made of a soft elastomeric material, such as food grade silicone rubber. The faceted nozzle 410 includes a tip 450 or apex which is the first portion of the faceted nozzle 410 to enter the user's nostril when attached to the vessel 100. At a center portion of the tip 450 is an outlet aperture 412 formed by a cylindrical wall 420.

Figure 9:
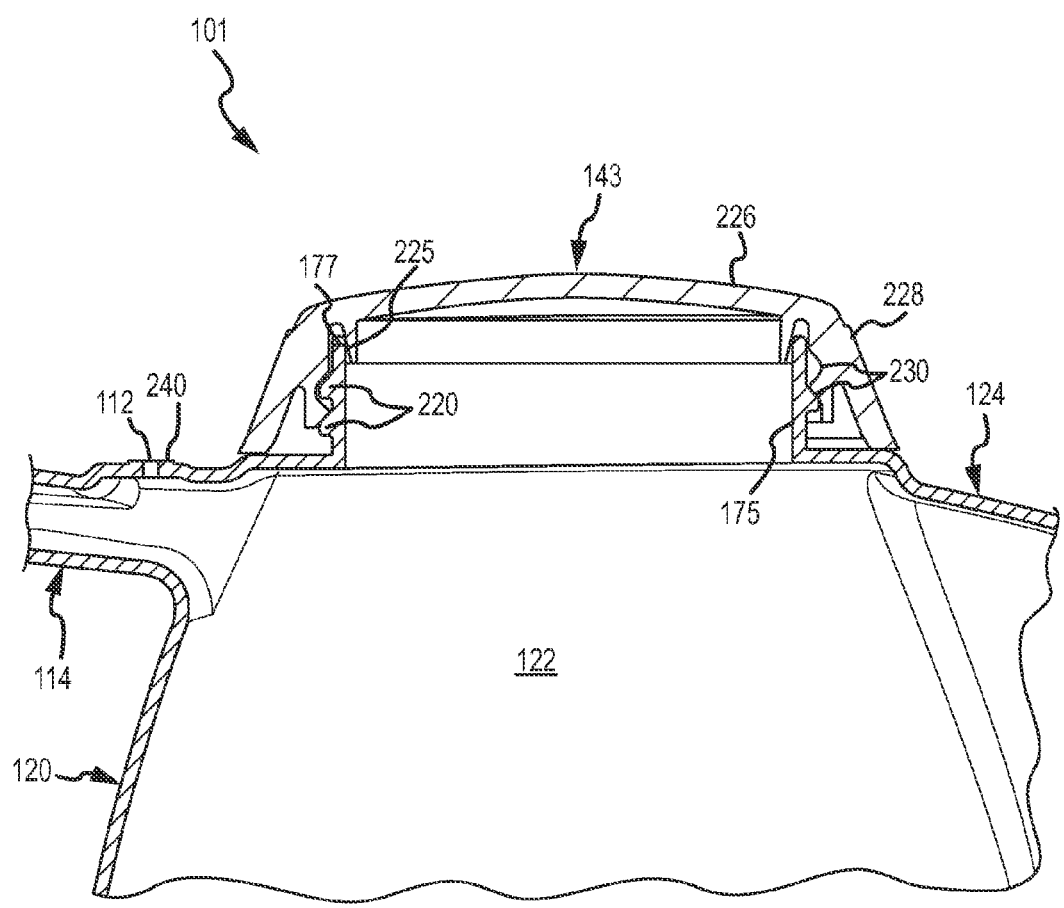
FIG. 9 is a cross-section view of an alternative lid and collar arrangement.

FIG. 9 shows a section view of a vessel 101 with an alternative lid 143 and collar 175 arrangement for providing a watertight and airtight seal in which the lid 143 includes a sealing element in the form of a lip seal 225 downwardly depending from the top portion 226 of the lid. The lip seal 225 tapers as it extends towards the main body 120 and has an annular arrangement proximate the internal sidewall forming the seal flange 228. The internal sidewall of the flange 228 and the tapering lip seal 225 form an area for receiving the terminal end 177 of the collar 175. Threads 230 are formed on the inner diameter of the seal flange 228 and correspond to the threads 220 on the collar 175 of the vessel 101 to form a threaded engagement and removably secure the lid 143 to the collar 175. When the lid 143 is fully threaded onto the collar 175 of the vessel 101, the lip seal 225 engaging the terminal end 177 of the collar 175 facilitates providing or creating an airtight and/or a watertight seal. The structures provided on vessel 101 are otherwise the same as on the vessel 100.

Figure 10:
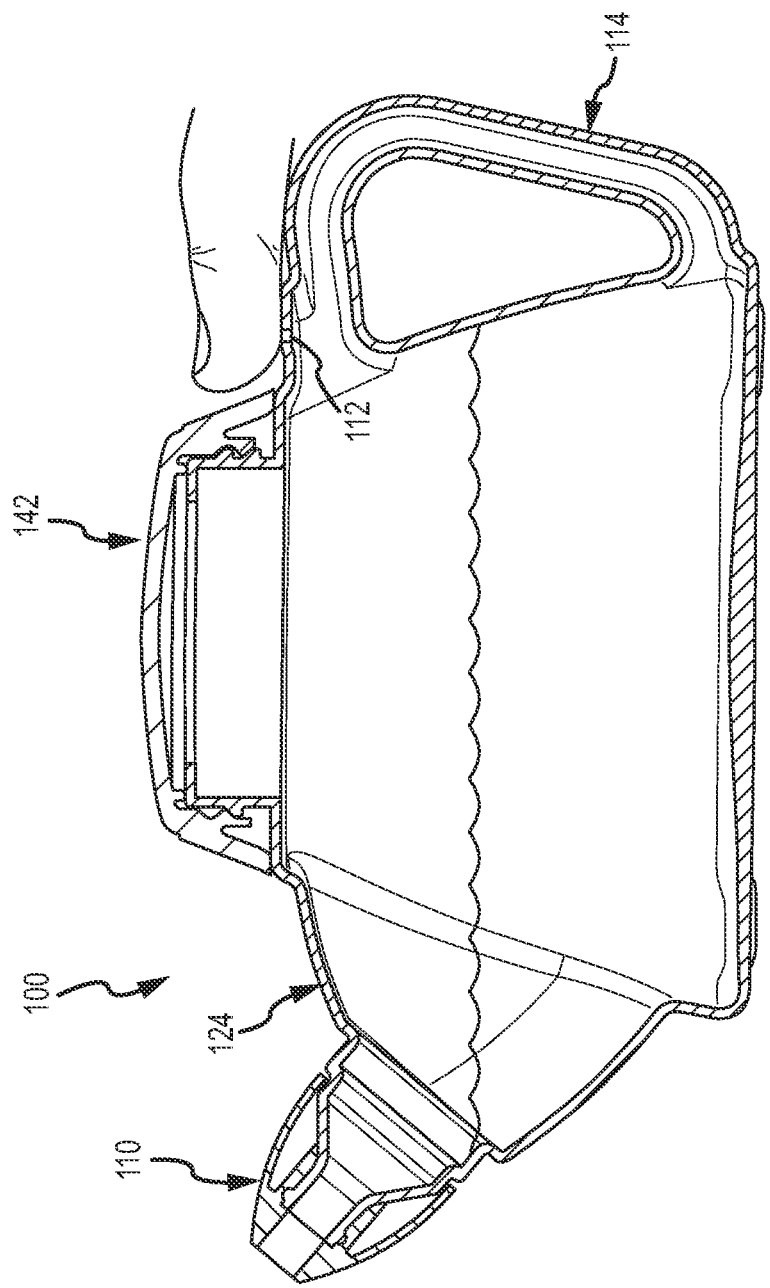
FIG. 10 is a cross-section view of the vessel of FIG. 1 with water or solution contained therein and a user's thumb positioned over the flow control aperture.
Figure 11:
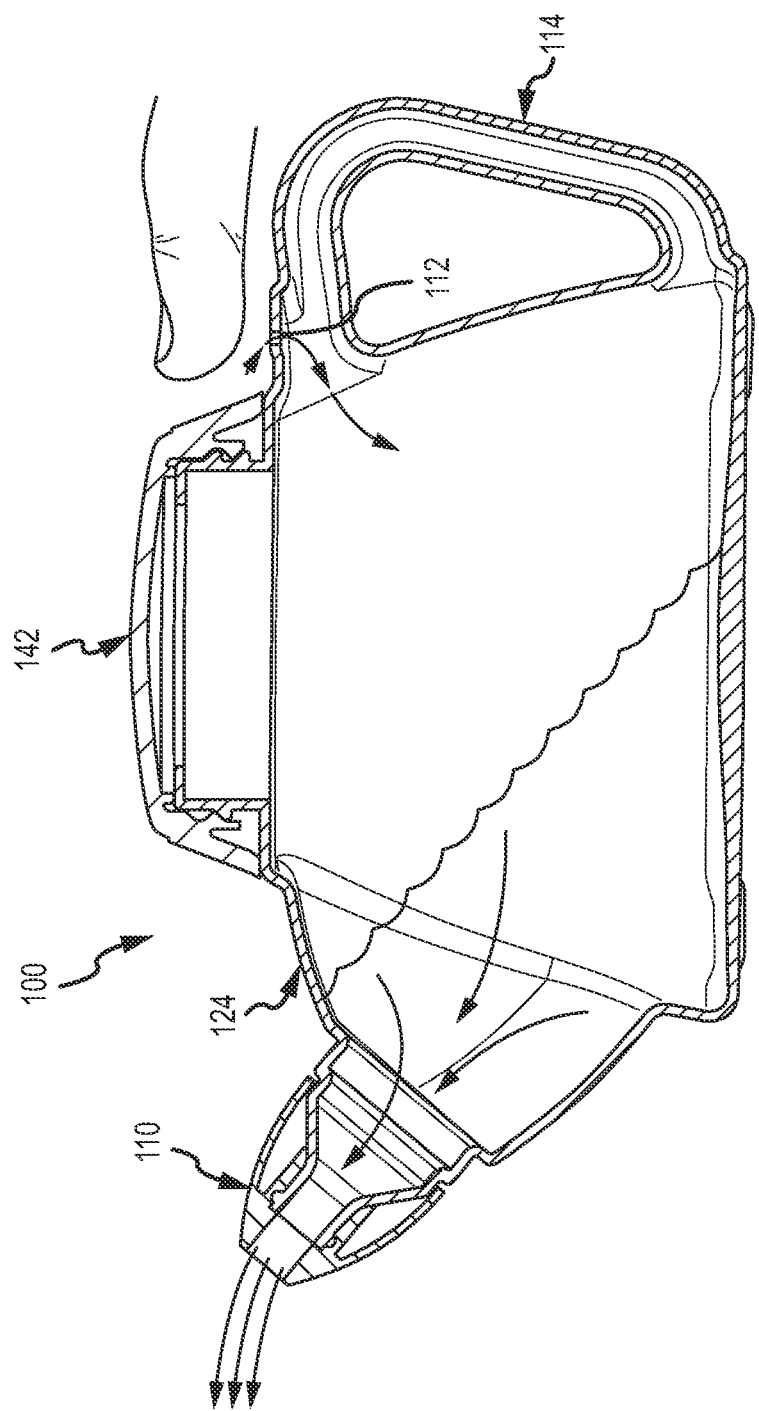
FIG. 11 is a cross-section view similar to FIG. 10 with the user's thumb disengaged from the flow control aperture and showing fluid passing through the nozzle.

FIGS. 10 and 11 show schematic cross-section views of the vessel 100 prior to and during use of the vessel for nasal rinse. FIG. 10 shows the vessel 100 having solution positioned therein with the solution not flowing through the nozzle 110, and with the user's thumb positioned over the aperture 112 to create a seal. In this configuration, while solution will flow through the nozzle 110 as the vessel is tipped, it is somewhat impeded by the lack of air flowing into the vessel 100 through the aperture 112 in order to backfill and release the vacuum formed by the water flowing through the nozzle 110.

During use, as shown in FIG. 11, when the user removes his thumb or finger from covering the aperture 112 in the handle, air enters the vessel 100 through the aperture 112 and the solution flows freely from the vessel 100 into the spout 124, through the end portion 148 of the spout into the fluid passageway in the end portion of the soft self-sealing nozzle 110 and out of the vessel 100 into the user's sinus for rinsing sinuses. To slow or stop the fluid flow from the nozzle 110, the user may seal the aperture 112 or partially cover the aperture 112 to allow some air to flow through the vessel 100. Because the vessel 101 depicted in FIG. 9 includes an aperture 112 and the vessel 101 is substantially sealed by except for the nozzle 110 when the user places their finger over the aperture 112, operating the vessel 101 is the same as the operation described above in connection with vessel 100.

It will be appreciated that where more than one aperture 112 is provided, the fluid flow from the nozzle 110 may have a first flow rate when all apertures are sealed, a second flow rate when one aperture 112 is unsealed, a third flow rate when two apertures are unsealed, and another flow rate when all apertures are unsealed in instances where more than two apertures are provided. In addition, where more than one aperture 112 is provided, the size and shape of the apertures may be the same or different allowing the user to select from multiple rates using different apertures. In implementations with more than one aperture, a the vessel 100, 101 may be provided with an additional cap (not shown) sized and shaped to be inserted into one aperture 112 thus allowing a user with small fingers to control the flow of fluid from the vessel using a single open aperture 112.

It is contemplated that the flow control aperture 112 may also be formed in the sidewall of the vessel 100, 101, for example at the back portion 136 of the main body in an area within reach of the user's fingers or thumb when holding the handle of the vessel.

Figure 12:
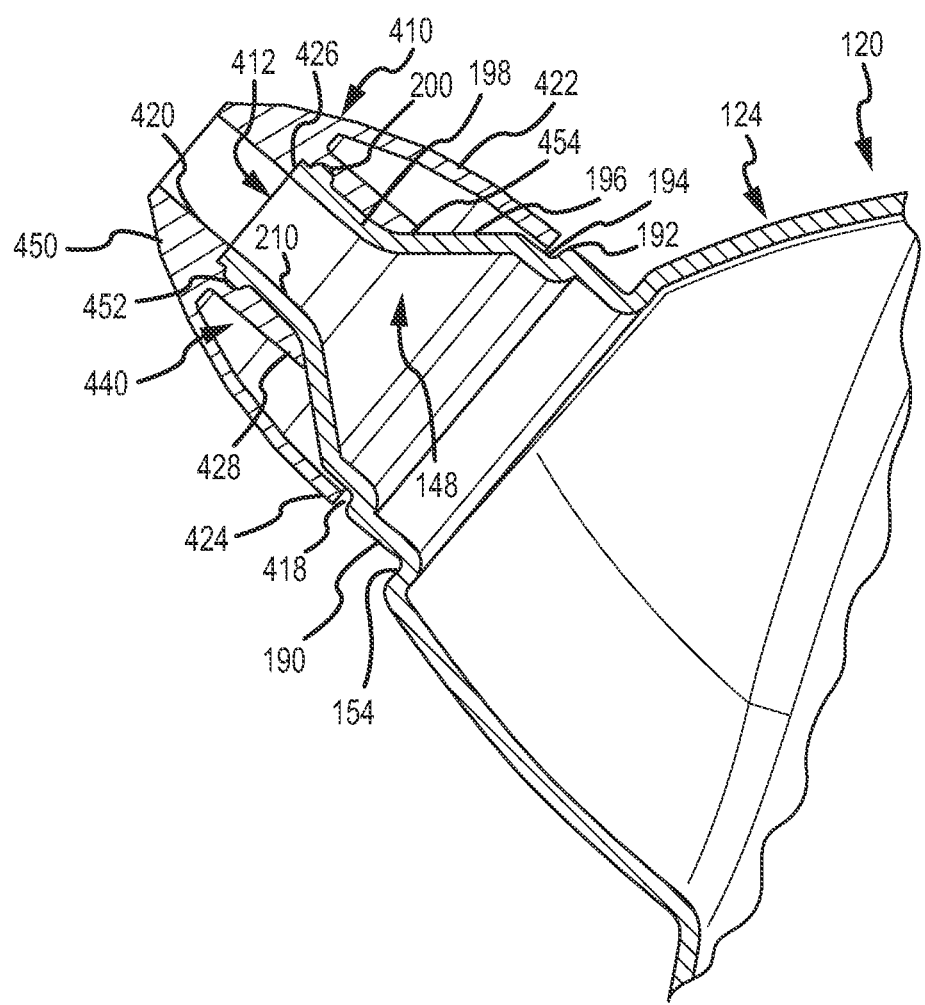
FIG. 12 is a cross-section view of the spout and nozzle of FIG. 6.

FIG. 12 is a cross-section view of the faceted nozzle 410 of FIG. 6 attached to the vessel 100 by the end portion 148 of the spout 124. The faceted nozzle 410 has a skirt 422 that extends outwardly and away from a tip 450, an inner collar 428 extending downwardly and away from the tip 450 and forms a cylindrical wall 420 creating a conduit or passageway within the inner surface of the faceted nozzle 410. The inner collar 428 may be formed integrally with the skirt 422. The inner collar 428 may terminate at the tip 450 creating the outlet aperture 412. The distal end of the inner collar 428 terminates inside the skirt 422. In some implementations the inner collar 428 may extend as far as the terminal edge 424 of the skirt 422 and in other implementations (e.g., the implementation illustrated in FIG. 12) the inner collar 428 may have a terminal edge 454 that terminates at a point above the terminal edge 424 of the skirt 422. In an exemplary embodiment, the wall thickness of the inner collar 428 may be approximately 0.060 inches.

As can be seen in FIG. 12, the inner collar 428 of the faceted nozzle 410 connects with the end portion 148 of the spout 124. The faceted nozzle 410 is placed above the end portion 148 and the end portion 148 may be inserted partially into the inner collar 428. In some implementations, the end portion 148 may extend only partially into the inner collar 428. Furthermore, an o-ring (not shown) may be secured within the annular recess 452 to create a fluid-tight seal between the inner collar 428 and the end portion 148.

The skirt 422 extends away from the second portion 198 and the inner collar 428 creating a void 440 or open space between the conical section 196 of the end portion 148 and the skirt 422. The void 440 or annular spacing is also formed between the skirt 422 and the inner collar 428, and the wall forming the skirt 422 extends further from the tip 450 than does the wall forming the inner collar 428 such that the terminal edge 424 of the skirt 422 is positioned around a cylindrical first portion 194 of the end portion 148. The void space 440 may be annular and may be continuous or discontinuous within the skirt wall.

The terminal edge 424 of the skirt 422, as well as the adjacent wall structure of the skirt 422, may closely fit with the cylindrical first portion 194 of the end portion 148 of the spout 124, but not necessarily engage with the cylindrical first portion 194. Also, a small gap 418 may be formed between the shoulder 192 of the end portion 148 and the terminal edge 424 of the skirt 422. As discussed above, the terminal edge 424 of the skirt 422 may not attach to or otherwise be affixed to the cylindrical first portion 194 and may move relative thereto. In other implementations the skirt 422 may rest along the cylindrical first portion 194 or otherwise contact the cylindrical first portion 194 of the end portion 148.

The inner collar 428 extends downward from the outlet aperture 412 and may mate and fluidly connect with the end portion 148 of the spout 124, attaching the faceted nozzle 410 to the main body 120. The inner collar 428 may include an annular recess 452 along its inner walls to receive the circumferential rib 200 on the second portion 198 of the end portion 148 of the spout 124. The terminal edge 454 of the inner collar 428 may be beveled at an angle complementary to the angle of the conical portion 196 of the spout 124 connect with the conical portion 196 and to provide additional sealing and help keep the fluid flowing through the end portion 148 and the faceted nozzle 410 and prevent fluid from passing between the engagement of the faceted nozzle 410 and the second portion 198.

The tip 450 of the faceted nozzle 410 above the annular recess 452 extends down to a cylindrical wall 420 that defines the outlet aperture 412 and the tip 450 may be thicker than the wall of the inner collar 428. The inner collar 428 may thus have a larger inner diameter than the cylindrical wall 420 forming the outlet aperture 412. A shoulder 426 formed in the tip 450 of the faceted nozzle 410 may be formed around the aperture 412 and engage with the end of the second portion 198 of the end portion 148 of the spout 124.

Figure 13A:
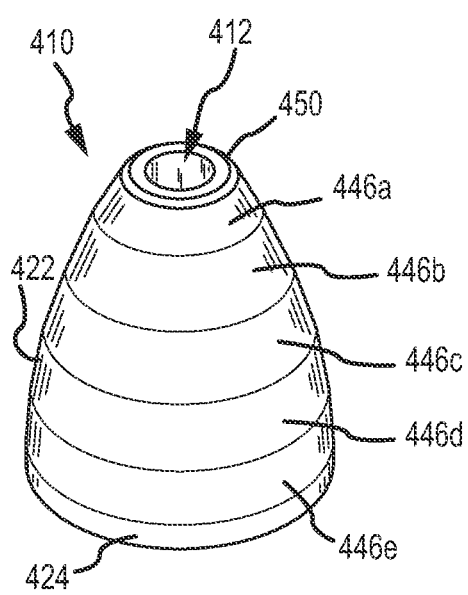
FIG. 13A is a top isometric view of the nozzle of FIG. 6 removed from the vessel.
Figure 13B:
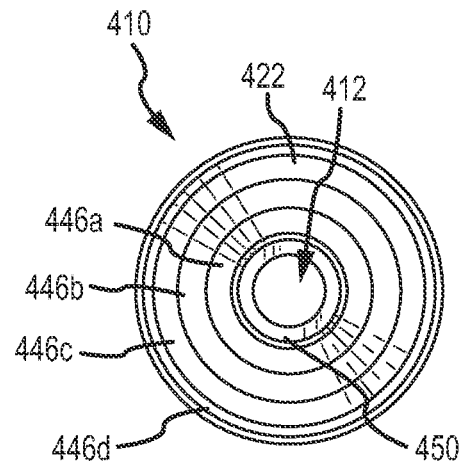
FIG. 13B is a top plan view of the nozzle illustrated in FIG. 13A.
Figure 13C:
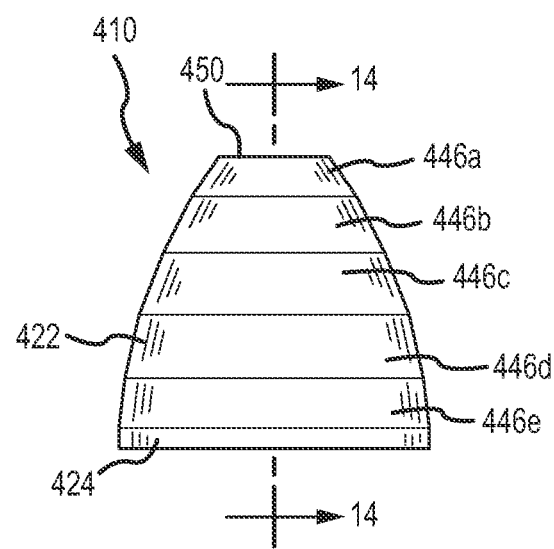
FIG. 13C is a side elevation view of the nozzle illustrated in FIG. 13A.
Figure 13D:
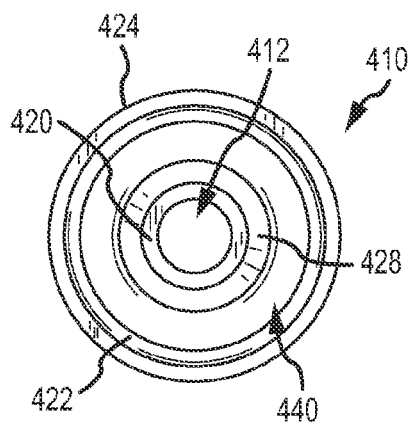
FIG. 13D is a bottom plan view of the nozzle illustrated in FIG. 13A.
Figure 13E:
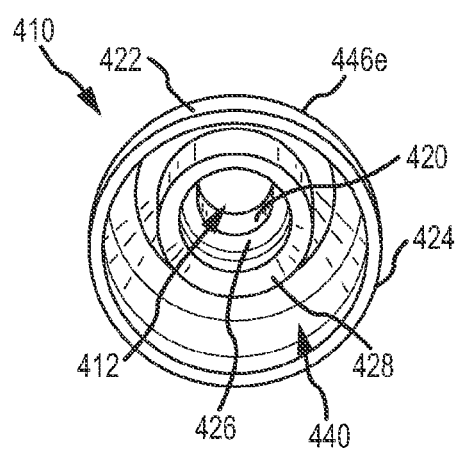
FIG. 13E is a bottom isometric view of the nozzle illustrated in FIG. 13A.
Figure 14:
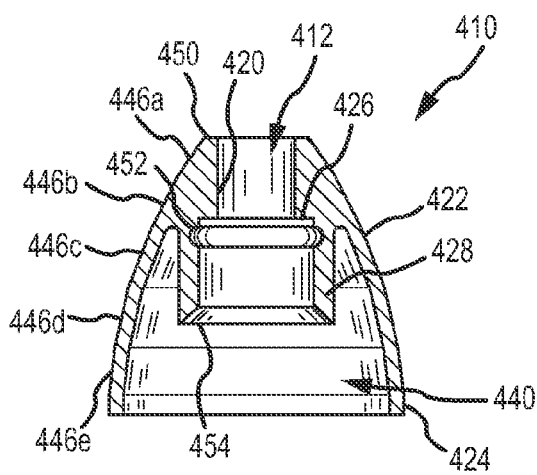
FIG. 14 is a cross-section view of the nozzle illustrated in FIG. 13A, viewed along line 14-14 in FIG. 13C.

FIG. 13A is a top isometric view of the faceted nozzle 410. FIG. 13B is a top plan view of the faceted nozzle 410. FIG. 13C is a side elevation view of the faceted nozzle 410; FIG. 13D is a bottom plan view of the faceted nozzle 410. FIG. 13E is a bottom isometric view of the faceted nozzle 410. FIG. 14 is a cross-section view of the faceted nozzle 410, as indicated by line 14-14 in FIG. 13C. Referring to FIGS. 13A-14, the faceted nozzle 410 is self-sealing and is made of a soft elastomeric material, for example, food grade silicone rubber. The nozzle 410 includes a tip 450 or apex which is the first portion of the nozzle 410 to enter the user's nostril when attached to the vessel 100, 101. At a center portion of the tip 450 is an outlet aperture 412.

A skirt 422 or body is formed by a wall extending downwardly and away from the tip 450, as can be see from FIG. 13A, the skirt 422 is faceted or stepped circumferentially, or otherwise made up of regions having flat extensions or mixed flat and curved extensions, as the skirt 422 extends downwards. In some exemplary implementations, the skirt 422 may have a wall thickness of approximately 0.040 inches.

The skirt 422 of the faceted nozzle 410 acts to form a seal with the user's nostril when the faceted nozzle 410 is attached to the vessel 100, 101. The skirt 422 includes steps 446a-446e, which create ridges on the outer surface of the skirt 422. In some implementations the steps 446a-446e may be approximately the same height; however, each step 446a-446e may have a different average or center diameter. In these implementations, each step 446a-446e increases the overall outer diameter of the skirt 422 and the faceted nozzle 410 maintains a generally rounded shape. For example, the first step 446a has a smaller average diameter than the second step 446b, and so on. In other implementations the steps 446a-446e may have different widths, such that the first step 446a may cover a greater portion of the outer surface of the skirt 422 than the second step 446b.

For example, as can be seen in FIG. 13A, the steps 446a-446e may be a series of stacked frustums having different outer wall angles. Each step 446a-446e is sloped at a predetermined angled and the outer wall has a larger diameter at the bottom edge of the steps 446a-446e than at the top edge of each step 446a-446e. In these implementations, each step 446a-446e decreases in diameter from the bottom edge to the top edge. Additionally, each step 446a-446e may have a different average diameter than the preceding step 446a-446e. This is because each step 446a-446e may have a different outer wall angle than the previous step 446a-446e. In some embodiments, the configuration of stacked frustum sections on top of one another may include ridges between each of the steps 446a-446e at the point of transition, from one step 446a-446e to the next, this gives the skirt 422 a faceted appearance and feel.

In these implementations, the user inserts the tip 450 into a user's nostril and then tips the vessel 100, 101, allowing the solution to travel from the main body 120 to the end portion 148 of the spout 124. Once the nasal solution enters the end portion 148, the solution enters the inner collar 428 proximate the tip 450 and exits into the nasal cavity via the outlet aperture 412. As the faceted nozzle 410 creates a seal between the nostril wall and the skirt 422 via the facets or steps 446a-

446e, the nasal solution is deposited into the nasal cavity without substantially leaking around the faceted nozzle 410 and the user's nostril.

While the tip 450 is be inserted into a user's nostril, one of the steps 446a-446e creates a seal between the faceted nozzle 410 and the nostril walls. The particular step 446a-446e that engages the user's nostril depends upon the size of the user's nostril. For example, the larger the user's nostril the lower the step 446a-446e may be that engages the nostril wall. The steps 446a-446e create a better seal than a purely rounded nozzle, as the steps 446a-446e better conform to the nostril wall—the nostril wall is not purely oval-shaped or conical-shaped—and the steps 446a-446e better mimic the inner surface of the nostril wall. It should be noted that although five steps 446a-446e have been illustrated, any number of steps 446a-446e may be included. The number of steps 446a-446e may be altered to create a smoother or rougher skirt 422. For example, depending on the desired sealing level the number of steps 446a-446e may be increased or decreased.

The skirt 422, when positioned in the user's nasal passage, flexes inwardly into the void 440 formed as the skirt 422 extends away from the connection between the faceted nozzle 410 and the second portion 198 of the end portion 148. As the skirt 422 flexes when sealing with the user's nostril, it may do so irregularly around its circumference in order to closely match the shape of the user's nostril. This helps create an adequate seal between the users nostril and the faceted nozzle 410 structure. When the faceted nozzle 410 is removed from the users nostril, the elastomeric material of the skirt 422 springs back into its original shape. Additionally, the gently curving, cone-like shape of the faceted nozzle 410 from the tip 450 down to the terminal edge 424 of the skirt 422 allows for a close fit with a variety of sizes of nasal passages.

The skirt 422 terminates at a terminal edge 424. In some embodiments the terminal edge 424 may be a continuation of the steps 446a-446e and in other embodiments the terminal edge 424 may extend past the steps 446a-446e creating a shoulder, flange, or the like. In these embodiments, the faceted nozzle 410 may be substantially free-standing along the skirt 422, i.e., the skirt 422 and/or other outer surfaces of the faceted nozzle 410 may be substantially unrestricted. As can be seen from FIG. 12, the terminal edge 424 is unrestricted by the first portion 194 of the end portion 148 of spout 124.

A variety of embodiments and variations of structures and methods are disclosed herein. Where appropriate, common reference numbers were used for common structural and method features. However, unique reference numbers were sometimes used for similar or the same structural or method elements for descriptive purposes. As such, the use of common or different reference numbers for similar or the same structural or method elements is not intended to imply a similarity or difference beyond that described herein.

The references herein to "up" or "top", "bottom" or "down", "lateral" or "side", and "horizontal" and "vertical", as well as any other relative position descriptor are given by way of example for the particular embodiment described and not as a requirement or limitation of the vessel or the apparatus and method for assembling the vessel. Reference herein to "is", "are", "should", "would", or other words implying a directive or positive requirement are intended to be inclusive of the permissive use, such as "may", "might", "could" unless specifically indicated otherwise.

The apparatus and associated method in accordance with the present invention has been described with reference to particular embodiments thereof. Therefore, the above description is by way of illustration and not by way of limitation. Accordingly, it is intended that all such alterations and variations and modifications of the embodiments are within the scope of the present invention as defined by the appended claims.

What is claimed is:

1. A vessel for use in rinsing a user's nasal passage comprising
a main body forming a cavity for receiving a fluid;
a spout extending off a front portion of the main body;
an elastomeric nozzle attached to the spout, the elastomeric nozzle having a tip and including
an inner collar for engagement with the spout, the inner collar extending downwardly from the tip; and
an outer skirt extending outwardly and downwardly from the tip, the outer skirt deflectable upon engagement with the walls of the user's nasal cavity, wherein the outer skirt extends further downwardly from the tip than the inner collar;
a handle extending off a back portion of the main body opposite the front portion, the handle being partially hollow and in communication with the cavity formed by the main body; and
an aperture formed in the handle in communication with the cavity by way of the partially hollow handle, said aperture for use in controlling a flow of the fluid positioned in the vessel out of the nozzle.

2. The vessel of claim 1, wherein the aperture is formed at a top portion of the handle.

3. The vessel of claim 1, wherein the aperture comprises a raised periphery extending from the handle.

4. The vessel of claim 1, wherein the outer skirt comprises a faceted outer surface.

5. The vessel of claim 1, wherein the main body includes an opening and a lid removably positioned over the opening and engageable with the main body to create a watertight seal between the lid and the main body.

6. The vessel of claim 5, wherein the lid comprises a sealing element for engaging with a top portion of the main body.

7. The vessel of claim 6, wherein the sealing element comprises a lip seal for engaging with a terminal end of a collar extending from the top portion of the main body.

8. The vessel of claim 1, wherein the spout comprises a rectangular top surface extending from the main body and an angled surface extending from the top surface, wherein the nozzle is received at an end portion of the spout, the end portion extending at a right angle from the angled surface.

9. The vessel of claim 8, wherein the end portion forms a conical section tapering down as the spout extends towards a spout portion forming a spout aperture, and the outer skirt is deflectable into a void space formed between the conical section and the outer skirt.

10. The vessel of claim 9, wherein the spout portion forming the spout aperture comprises an annular rib around an external circumference configured to detachably couple with an annular channel of the nozzle.

11. The vessel of claim 10, wherein the annular channel of the nozzle is formed in an inner collar of the nozzle, and the inner collar forms a nozzle aperture such that fluid positioned in the vessel flows from the spout aperture and out of the nozzle through the nozzle aperture.

12. The vessel of claim 1, wherein the outer skirt is spaced away from the inner collar along at least a portion of its length.

13. The vessel of claim 12, wherein a void space is formed between the outer skirt and the inner collar, and the outer skirt is deflectable into the void space.

14. The vessel of claim 13, wherein the spout forms a conical section adjacent to the outer skirt such that another void space is formed between the outer skirt and the conical section beyond a terminal edge of the inner collar, and the outer skirt is deflectable into the another void space.

15. The vessel of claim 14, wherein the skirt includes a terminal edge which engages a cylindrical portion of the spout adjacent to the terminal edge, wherein the cylindrical portion is proximate the main body and the conical section extends distally from the cylindrical portion.

16. A vessel for use in rinsing a user's nasal passage comprising
a main body forming a cavity for receiving a fluid and an opening for allowing the fluid to enter the cavity;
a lid removably positioned over the opening and engageable with the main body to create a watertight seal between the lid and the main body;
a spout extending off the main body;
an elastomeric nozzle detachably coupled to the spout, the elastomeric nozzle having a tip and defining
an inner collar for engagement with the spout, the inner collar extending downwardly from the tip; and
an outer skirt extending outwardly and downwardly from the tip, the outer skirt deflectable upon engagement with the walls of the user's nasal cavity, wherein the outer skirt extends further downwardly from the tip than the inner collar;
a handle extending off the main body, the handle being at least partially hollow and in communication with the cavity formed by the main body;
an aperture formed in a top portion of the handle in communication with the cavity by way of the at least partially hollow handle, said aperture for use in controlling a flow of the fluid in the main body out of the nozzle; and
an annular raised periphery surrounding the aperture and extending from the top portion of the handle, said raised periphery for facilitating sealing of the aperture with the user's finger.

17. The vessel of claim 16, wherein an outer surface of the outer skirt is faceted.

18. The vessel of claim 17, wherein the spout forms a conical section tapering down as the spout extends towards a spout portion forming a spout aperture, and the nozzle is detachably coupled to said spout portion.

19. The vessel of claim 18, wherein the outer skirt is deflectable into a void space formed between the conical section and the outer skirt.

20. The vessel of claim 17, wherein the outer skirt is comprised of at least two frustum sections stacked in series on top of one other, wherein the first frustum section has an average larger diameter than the second frustum section.

21. The vessel of claim 1, wherein the outer skirt surrounds the inner collar and is spatially separated from the inner collar defining a void space between the outer skirt and the inner collar.

22. The vessel of claim 1, wherein an outer surface of the outer skirt of the nozzle is in a form of a plurality of stacked frustums defining a faceted surface.

23. The vessel of claim 22, wherein the plurality of stacked frustums comprises a first frustum, a second frustum positioned on top of the first frustum, and a third frustum positioned on top of the second frustum.

24. The vessel of claim 23, wherein
a first inflection point is defined at an intersection between the first frustum and the second frustum; and
a second inflection point is defined at an intersection between the second frustum and the third frustum.

25. The vessel of claim 24, wherein
the first frustum has a first tangent that includes a top edge of the frustum and the first inflection point and intersects with a center axis of the nozzle to form a first angle;
the second frustum has a second tangent that that includes the first inflection point and the second inflection point and intersects with a center axis of the nozzle to form a second angle;
the third frustum has a third tangent that includes the second inflection point and a bottom edge of the third frustum and intersects with a center axis of the nozzle to form a third angle;
the first angle is large than the second angle; and
the second angle is larger than the third angle.

* * * * *

UNITED STATES PATENT AND TRADEMARK OFFICE
CERTIFICATE OF CORRECTION

| | | |
|---|---|---|
| PATENT NO. | : 8,486,029 B2 | Page 1 of 1 |
| APPLICATION NO. | : 12/970610 | |
| DATED | : July 16, 2013 | |
| INVENTOR(S) | : Cacka et al. | |

It is certified that error appears in the above-identified patent and that said Letters Patent is hereby corrected as shown below:

In the Claims

Claim 25, Column 14, Line 30: remove "that" before "includes"

Claim 25, Column 14, Line 38: replace "large" with "larger"

Signed and Sealed this
Eighth Day of April, 2014

Michelle K. Lee
*Deputy Director of the United States Patent and Trademark Office*